(12) United States Patent
Wang et al.

(10) Patent No.: US 12,369,877 B2
(45) Date of Patent: Jul. 29, 2025

(54) IMAGE ACQUISITION WITH MULTIPLE DETECTORS

(71) Applicant: CARESTREAM HEALTH, INC., Rochester, NY (US)

(72) Inventors: Xiaohui Wang, Pittsford, NY (US); Jangho Park, Fairport, NY (US); David Y. Chan, Vaughan (CA)

(73) Assignee: Carestream Health, Inc., Rochester, NY (US)

( * ) Notice: Subject to any disclaimer, the term of this patent is extended or adjusted under 35 U.S.C. 154(b) by 356 days.

(21) Appl. No.: 17/776,646

(22) PCT Filed: Dec. 8, 2020

(86) PCT No.: PCT/US2020/063734
§ 371 (c)(1),
(2) Date: May 13, 2022

(87) PCT Pub. No.: WO2021/118969
PCT Pub. Date: Jun. 17, 2021

(65) Prior Publication Data
US 2022/0401055 A1     Dec. 22, 2022

Related U.S. Application Data

(60) Provisional application No. 62/946,475, filed on Dec. 11, 2019.

(51) Int. Cl.
*A61B 6/00*     (2024.01)
*A61B 6/42*     (2024.01)

(52) U.S. Cl.
CPC ............ *A61B 6/545* (2013.01); *A61B 6/4233* (2013.01); *A61B 6/5211* (2013.01); *A61B 6/547* (2013.01); *A61B 6/563* (2013.01); *A61B 6/4405* (2013.01)

(58) Field of Classification Search
CPC ..... A61B 6/545; A61B 6/4233; A61B 6/5211; A61B 6/547; A61B 6/563; A61B 6/4405
See application file for complete search history.

(56) References Cited

U.S. PATENT DOCUMENTS

2015/0245807 A1* 9/2015 Tajima ................ A61B 6/5294
                                                        378/98
2017/0352154 A1* 12/2017 Tezuka ................ A61B 5/0013
2018/0000442 A1* 1/2018 Hiroike .................... A61B 6/54

OTHER PUBLICATIONS

International Search Report mailed Mar. 12, 2021 for International Application No. PCT/US2020/063734, 2 Pages.

* cited by examiner

*Primary Examiner* — Carolyn Fin (57) ABSTRACT

A radiography system having multiple digital radiographic detectors captures an image in each of the detectors when the x-ray source is fired. The detectors evaluate the captured images and a controller prioritizes the captured images according to the evaluations to determine which captured images are forwarded and in what order. At least one of the DR detectors captures a suitable diagnostic x-ray image.

11 Claims, 7 Drawing Sheets

| Detector ID | Registered | Status | Activate |
|---|---|---|---|
| (1) xxyy-yyyy | Yes | Active | X |
| (2) zzzz-yyyy | Yes | Disconnected | |
| (3) zzxx-yyyy | No | Available | |
| (4) xxzz-yyyy | Yes | Active | X |
| (5) xxxx-yyzz | Yes | Active | |

IMAGE ACQUISITION WITH MULTIPLE DETECTORS

CROSS REFERENCE TO RELATED APPLICATIONS

This application claims the benefit of and is a U.S. National Phase filing of PCT Application PCT/US2020/063734 filed Dec. 8, 2020 entitled "IMAGE ACQUISITION WITH MULTIPLE DETECTORS", in the name of Wang et al., which claims benefit of U.S. Patent Application Ser. No. 62/946,475, filed Dec. 11, 2019, in the name of Wang et al., and entitled IMAGE ACQUISITION WITH MULTIPLE DETECTORS.

DETAILED DESCRIPTION OF THE INVENTION

This application claims priority to U.S. Patent Application Ser. No. 62/946,475, filed Dec. 11, 2019, in the name of Wang, et al., and entitled IMAGE ACQUISITION WITH MULTIPLE DETECTORS, which is hereby incorporated by reference herein in its entirety.

BACKGROUND OF THE INVENTION

The subject matter disclosed herein relates to stationary or mobile x-ray imaging systems used in medical imaging facilities that have one or more digital radiography detectors assigned or registered thereto for use in capturing x-ray images.

A problem that may occur during x-ray imaging using DR detectors is that radiographic images may not be properly captured during an x-ray exposure due to a mismatch between the detector being used for image capture and the detector actually capturing the exposures.

The discussion above is merely provided for general background information and is not intended to be used as an aid in determining the scope of the claimed subject matter.

BRIEF DESCRIPTION OF THE INVENTION

A system and method is disclosed herein to simultaneously activate, or arm, all DR detectors that are assigned to a particular radiography system and are thereby activated for image capture at the moment when the x-ray source of the system is fired to expose a subject for radiographic imaging.

The activation of the DR detectors can be initiated by one of, or a combination of, several user actions: removal of the detector from a storage slot; moving the detector which triggers a movement sensor; and moving the detector which triggers a proximity sensor detecting that the detector is moving away from a particular storage location. The activation of the detectors would include initially awakening the detectors from an idle mode or a low power sleep mode to a ready mode for x-ray exposure integration, and/or starting a standard integration cycle performed by the DR detector. Once an exposure(s) is captured, the system can set the detectors back into an idle mode or low power sleep mode for the purpose of preserving battery energy or reducing generated heat. As multiple radiographic images are captured by the activated DR detectors, the captured images may be transferred to the system console, or displayed on digital displays built into the DR detectors, and presented to an operator to select the effective image for diagnostic use and to discard any remaining images. An alternative method may include the console, or the DR detectors, automatically processing the captured images to select and store those images that most are likely to be used effectively for diagnosis. Another alternative method is to program the DR detectors to process the captured images and report the image attributes, such as average or maximum signal magnitude, to the console system, or to an on-board processing system, before the images are finalized, selected for diagnosis, or transmitted to the console. The console may also be used to determine which detectors will transfer a captured image first, second, third, et al., based on reported signal magnitudes or other data recorded by the DR detectors.

A radiography system having multiple digital radiographic detectors captures an image in each of the detectors when the x-ray source is fired. The detectors record data pertaining to the image capture and evaluate the captured images. A controller prioritizes the captured images according to the evaluations or according to the recorded data to determine which captured images are forwarded, and if more than one captured image is forwarded then in which order they are transmitted. At least one of the DR detectors captures a suitable diagnostic x-ray image. An advantage that may be realized in the practice of some disclosed embodiments of the invention is to ensure properly capturing an x-ray image during an x-ray examination.

In one embodiment, a radiography system having an x-ray source and a plurality of DR detectors is configured to capture an image in each of the DR detectors in synchronization with activating the x-ray source. The plurality of detectors are further configured to transmit one or more of the captured images according to a priority order.

In another embodiment, a method of operating a radiography system includes firing an x-ray source and capturing an image in each of a plurality of DR detectors. The detectors are prioritized in a sequential order and at least one of the plurality of DR detectors forwards its captured image to the system according to the prioritized order.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

Figure 1:
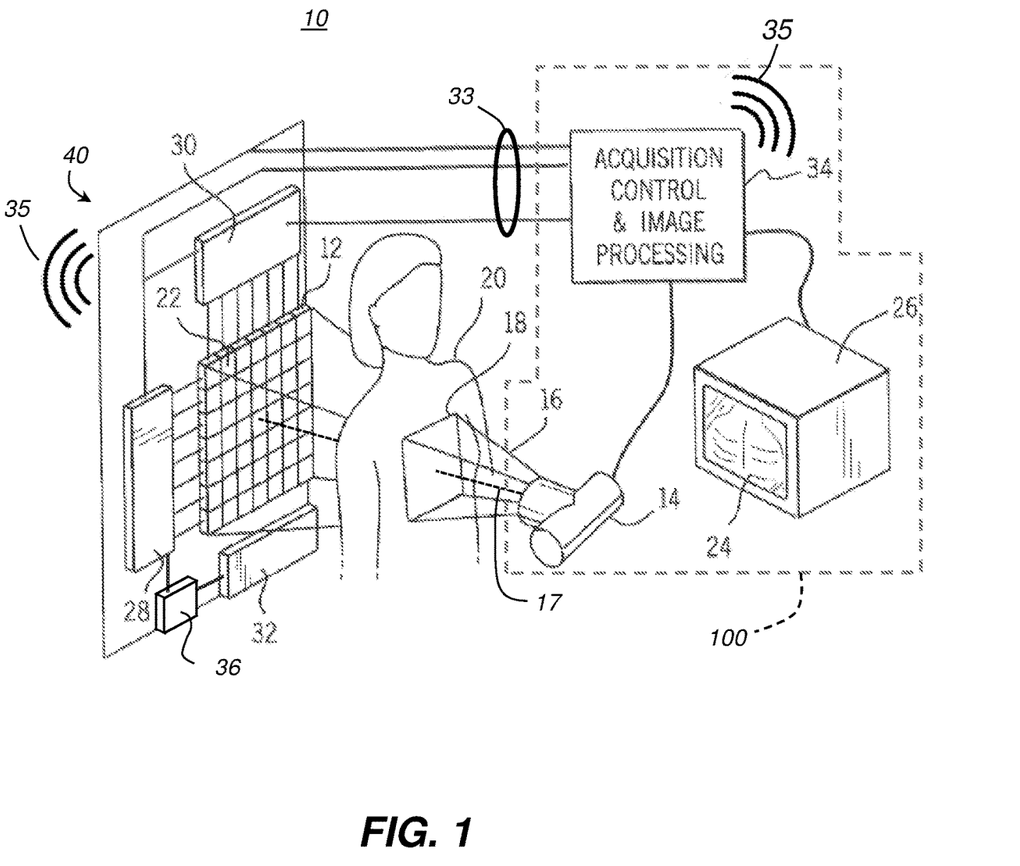
FIG. 1 is a schematic perspective view of an exemplary x-ray system.

FIG. 1 is a perspective view of a digital radiographic (DR) imaging system 10 that may include a generally curved or planar DR detector 40 (shown in a planar embodiment and without a housing for clarity of description), an x-ray source 14 configured to generate radiographic energy (x-ray radiation), and a digital monitor, or electronic display, 26 configured to display images captured by the DR detector 40, according to one embodiment. The digital monitor, or electronic display, 26 may comprise a touch screen to enable a user to enter instructions for operating the digital radiographic (DR) imaging system 10. The DR detector 40 may include a two dimensional array 12 of detector cells 22 (photosensors), arranged in electronically addressable rows and columns. The DR detector 40 may be positioned to receive x-rays 16 passing through a subject 20 during a radiographic energy exposure, or radiographic energy pulse, emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the array 12 of photosensitive detector cells 22. The curved or planar DR detector 40 is positioned, as much as possible, in a perpendicular relation to a substantially central ray 17 of the plurality of rays 16 emitted by the x-ray source 14. In a curved array embodiment, the source 14 may be centrally positioned such that a larger percentage, or all, of the photosensitive detector cells are positioned perpendicular to incoming x-rays from the centrally positioned source 14. The array 12 of individual photosensitive cells (pixels) 22 may be electronically addressed (scanned) to determine a signal level captured therein by their position according to column and row, which signal level datum may be processed individually, as a whole image using the entire array of photosensitive cells, or with respect to a portion of the array, as needed. As used herein, the terms "column" and "row" refer to the vertical and horizontal arrangement of the photosensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array signal levels, 12 may be transmitted to electronic read-out circuit 30. Each photosensitive cell 22 may independently store a charge proportional to an intensity, signal level, or energy level, of the attenuated radiographic radiation, or x-rays, received and absorbed in the cell, Thus, each photosensitive cell, when read-out, provides information defining a pixel of a radiographic image 24, e.g. a brightness level or an amount of energy absorbed by the pixel, that may be digitally decoded by on-board image processing electronics 36, which may be referred to herein as a controller, processor, or processing system, or may be transmitted to a central acquisition control and image processor 34, which may be referred to herein as a controller, for display on a digital monitor 26 for viewing by a user. An electronic bias circuit 32 is electrically connected to the two-dimensional detector array 12 to provide a bias voltage to each of the photosensitive cells 22.

Figure 4:
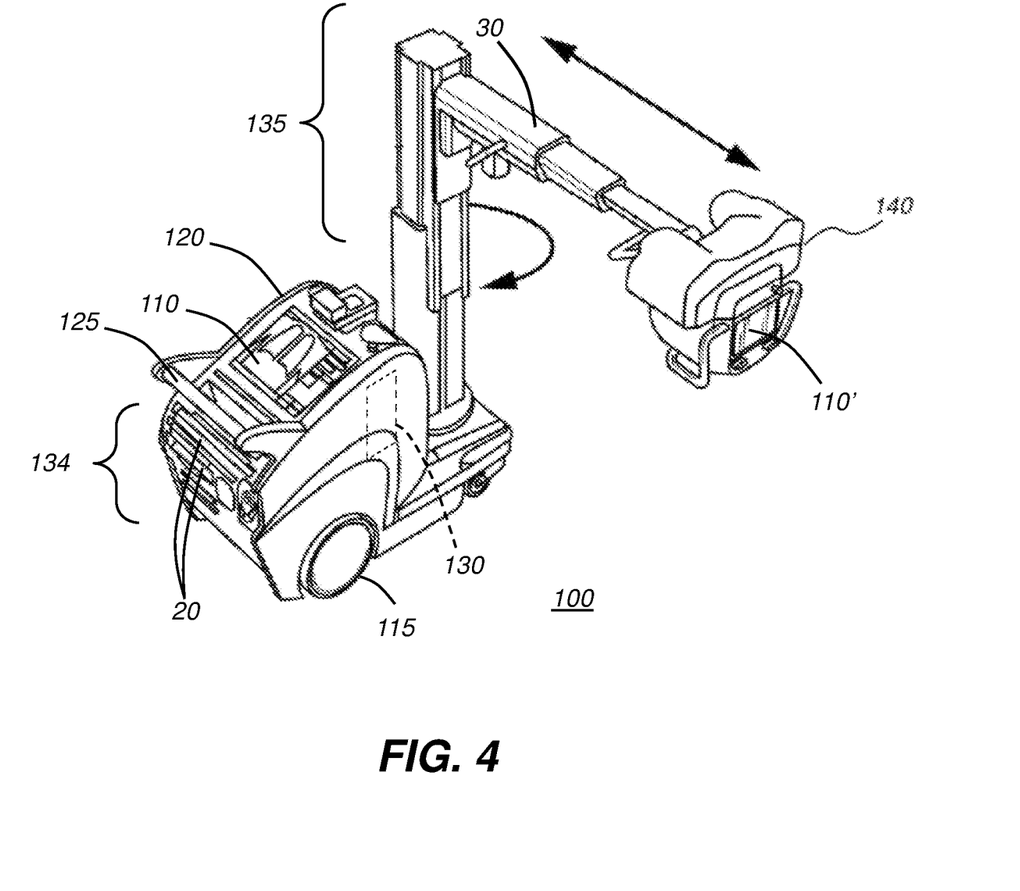
FIG. 4 is an illustration of a mobile radiography system inch a storage to multiple DR detectors.

Each of the bias circuit 32, the scanning circuit 28, and the read-out circuit 30, may communicate electronically and be controlled by on-board processor 36. Each of the bias circuit 32, the scanning circuit 28, and the read-out circuit 30, may also communicate with external acquisition control and image processing unit 34 over a connected cable 33 (wired), or the DR detector 40 and the acquisition control and image processing unit 34 may each be equipped with a wireless transmitter and receiver to transmit radiographic image data wirelessly 35 to the acquisition control and image processing unit 34. The acquisition control and image processing unit 34 may include a processor and electronic memory (not shown) to control operations of the DR detector 40 as described herein, including control of circuits 28, 30, and 32, for example, by use of programmed instructions, and to store and process image data. The acquisition control and image processing unit 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16. A portion or all of the acquisition control and image processing unit 34 functions may reside in the detector 40 in the on-board processing system 36 which may include a processor and electronic memory to control operations of the DR detector 40 as described herein, including control of circuits 28, 30, and 32, by use of programmed instructions, and to store and process image data similar to the functions of standalone external acquisition control and image processing system 34. The image processing system may perform image acquisition and image disposition functions as described herein. The image processing system 36 may control image transmission, image processing and image correction on board the detector 40 based on instructions or other commands transmitted from the acquisition control and image processing unit 34, and transmit corrected digital image data therefrom. Alternatively, acquisition control and image processing unit 34 may receive raw image data from the detector 40 and process the image data for storage, or it may store raw unprocessed image data in local memory, or in remotely accessible memory. As described herein below, x-ray source 14, digital monitor 26, and acquisition control and image processing system 34, may be contained in and form part of a mobile radiography apparatus 100 (FIG. 4).

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the DR detector 40 may include an indirect or direct type of DR detector, Examples of sensing elements used in sensing array 12 include various types of photoelectric conversion devices (e.g., photosensors) such photodiodes (P-N or PIN diodes), photo-capacitors (MIS), phototransistors or photoconductors. Examples of switching elements used for signal read-out include a-Si TFTs, oxide TFTs, MOS transistors, bipolar transistors and other p-n junction components.

Figure 2:
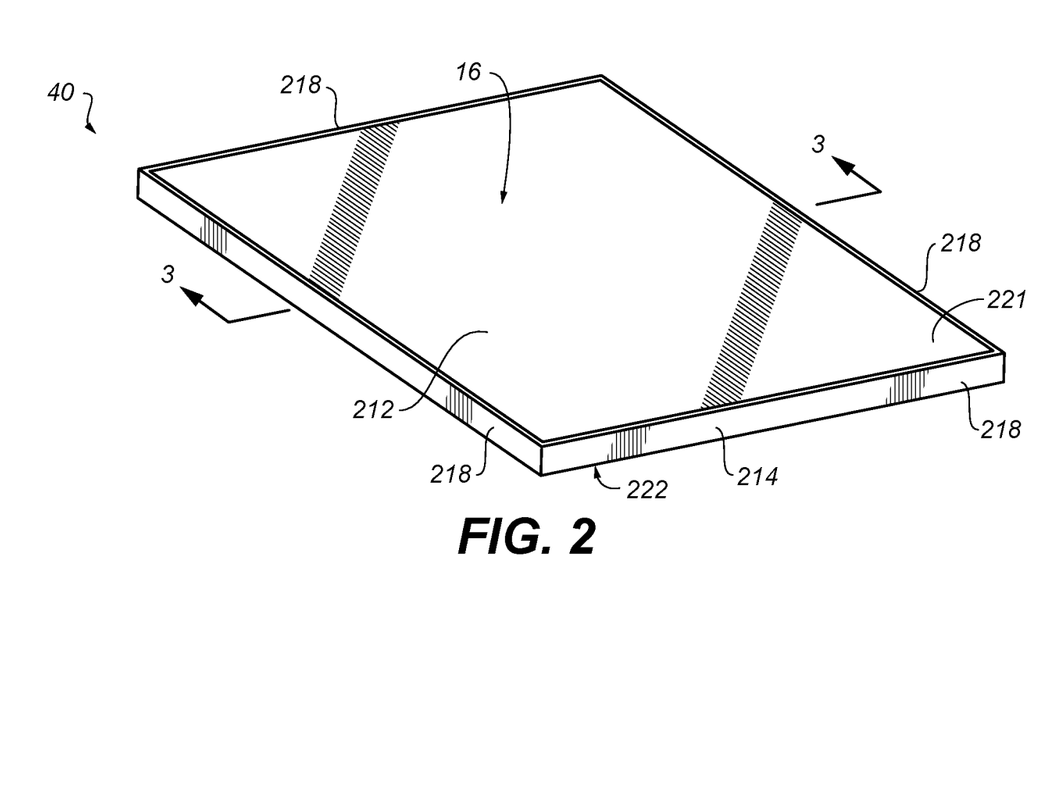
FIG. 2 is a diagram of an exemplary DR detector.

FIG. 2 shows a perspective view of generally rectangular, planar, portable wireless DR detector 40 according to an embodiment of DR detector 40 disclosed herein. The DR detector 40 may include a flexible substrate to allow the DR detector to be bent into a curved orientation. The flexible substrate may be fabricated in a permanent curved orientation, or it may remain flexible throughout its life to provide an adjustable curvature in two or three dimensions, as desired. The DR detector 40 may include a similarly flexible housing portion 214 that surrounds a multilayer structure comprising a flexible photosensor array portion 22 of the DR detector 40. The housing portion 214 of the DR detector 40 may include a continuous, rigid or flexible radiopaque material, surrounding an interior volume of the DR detector 40. The housing portion 214 may include four flexible edges 218, extending between the top side 221 and the bottom side 222, and arranged substantially orthogonally in relation to the top and bottom sides 221, 222. The bottom side 222 may be continuous with the four edges and disposed opposite the top side 221 of the DR detector 40. The top side 221 comprises a top cover 212 attached to the housing portion 214 which, together with the housing portion 214, substantially encloses the multilayer structure in the interior volume of the DR detector 40. The top cover 212 may be attached to the housing 214 to form a seal therebetween, and be made of a material that passes x-rays 16 without significant attenuation thereof, i.e., a radiolucent material, such as a carbon fiber plastic, polymeric, or other plastic based material.

Figure 3:
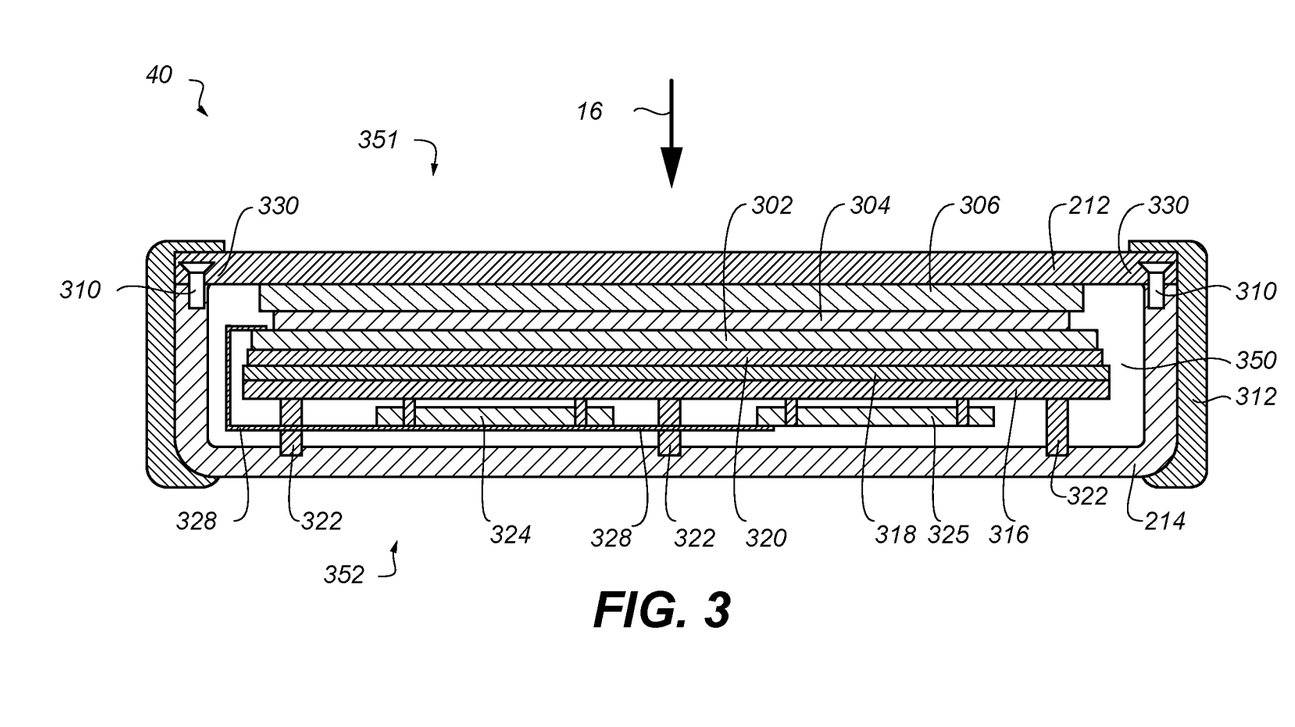
FIG. 3 is a cross section diagram of an exemplary DR detector.

With reference to FIG. 3, there is illustrated in schematic form an exemplary cross-section view along section 3-3 of the exemplary embodiment of the DR detector 40. For spatial reference purposes, one major surface of the DR detector 40 may be referred to as the top side 351 and a second major surface may be referred to as the bottom side 352, as used herein. The multilayer structure may be disposed within the interior volume 350 enclosed by the housing 214 and top cover 212 and may include a flexible curved or planar scintillator layer 304 over a curved or planar the two-dimensional imaging sensor array 12 shown schematically as the device layer 302. The scintillator layer 304 may be directly under (e.g., directly connected to) the substantially planar top cover 212, and the imaging array 302 may be directly under the scintillator 304. Alternatively, a flexible layer 306 may be positioned between the scintillator layer 304 and the top cover 212 as part of the multilayer structure to allow adjustable curvature of the multilayer structure and/or to provide shock absorption. The flexible layer 306 may be selected to provide an amount of flexible support for both the top cover 212 and the scintillator 304, and may comprise a foam rubber type of material. The layers just described comprising the multilayer structure each may generally be formed in a rectangular shape and defined by edges arranged orthogonally and disposed in parallel with an interior side of the edges 218 of the housing 214, as described in reference to FIG. 2.

A substrate layer 320 may be disposed under the imaging array 302, such as a rigid glass layer, in one embodiment, or flexible substrate comprising polyimide or carbon fiber upon which the array of photosensors 302 may be formed to allow adjustable curvature of the array, and may comprise another layer of the multilayer structure. Under the substrate layer 320 a radiopaque shield layer 318 may be used as an x-ray blocking layer to help prevent scattering of x-rays passing through the substrate layer 320 as well as to block x-rays reflected from other surfaces in the interior volume 350. Readout electronics, including the scanning circuit 28, the read-out circuit 30, the bias circuit 32, and processing system 36 (all of FIG. 1) may be formed adjacent the imaging array 302 or, as shown, may be disposed below frame support member 316 in the form of integrated circuits (ICs) electrically connected to printed circuit boards 324, 325. Other electronic modules disposed below frame support member 316 may include a bluetooth communication module for near field communication and an accelerometer for sensing movement of the detector 40. The imaging array 302 may be electrically connected to the readout electronics 324 (ICs) over a flexible connector 328 which may comprise a plurality of flexible, sealed conductors known as chip-on-film (COF) connectors.

X-ray flux may pass through the radiolucent top panel cover 212, in the direction represented by an exemplary x-ray beam 16, and impinge upon scintillator 304 where stimulation by the high-energy x-rays 16, or photons, causes the scintillator 304 to emit lower energy photons as visible light rays which are then received in the photosensors of imaging array 302. The frame support member 316 may connect the multilayer structure to the housing 214 and may further operate as a shock absorber by disposing elastic pads (not shown) between the frame support beams 322 and the housing 214. Fasteners 310 may be used to attach the top cover 212 to the housing 214 and create a seal therebetween in the region 330 where they come into contact, in one embodiment, an external bumper 312 may be attached along the edges 218 of the DR detector 40 to provide additional shock-absorption.

FIG. 4 shows a perspective view of a mobile radiography unit 100 that can be used together with portable DR detectors 40 that are mechanically uncoupled from the mobile radiography unit 100. The exemplary mobile x-ray or radiographic apparatus 100 can be employed for digital radiography (DR) and/or tomosynthesis or tomographic imaging. Mobile radiography apparatus 100 can include a moveable transport frame 120 that includes a first digital display 110 and an optional second digital display 110', as part of x-ray tube head 140, to display relevant information such as obtained x-ray images and related data, as well as to receive operator inputs to control firing an x-ray source in x-ray tube head 140. As shown in FIG. 4, the second display 11' can be pivotably mounted at the x-ray tube head 140 to be viewable/touchable from a 360 degree area.

The displays 110, 110' can provide an input screen (e.g., touch screens) for an operator to implement or control functions of the mobile radiography apparatus 100, such as controlling firing and energy level of an x-ray source in tube head 140, adjusting an aperture of a collimator in tube head 140, registering DR detectors with mobile radiography apparatus 100, generating, storing, transmitting, modifying, and printing of the obtained, or captured x-ray image(s). For mobility, the mobile radiographic apparatus 100 can have one or more wheels 115 and one or more handle grips 125, typically provided at waist-level, arm-level, or hand-level, that help an operator to move and to guide the mobile radiographic apparatus 100 to its intended location. A self-contained battery pack (e.g., rechargeable) can provide source power, which can reduce or eliminate the need for operation near a power outlet. Further, the self-contained battery pack can be configured to provide power for motorized wheels to transport the entire mobile radiography unit 100 to its intended location. For storage, the mobile radiographic apparatus 100 can include slots 134 for storing one or more DR detectors 40 or computed radiography cassettes. The slots 134 can be a storage area disposed in the transport frame 120 configured to removably retain at least one DR detector 40. The storage slots 134 can be configured to hold a plurality of detectors 40 and can also be configured to hold one size or multiple sizes of DR detectors.

Still referring to FIG. 4, a processing control system 130, which may be referred to herein as a controller, provides the control logic for image processing, identification of DR detectors registered to the mobile radiography apparatus 100, identifying a position of the tube head 140 relative to the transport frame 120, as well as other control functions. Image processing may be provided by the processing control system 130 as part of mobile radiography apparatus 100 itself, or it can be provided by one or more external computers, such as a control console, and other processors networked in signal communication with mobile radiography apparatus 100.

Mounted to frame 120 is a support member or column 135 that supports x-ray head 140, also called an x-ray tube, tube head, or generator, that includes the x-ray source and that can be mounted to the support member or column 135. In the embodiment shown in FIG. 4, the support member or column 135 can include a second horizontal telescoping section 30 that extends outward at a fixed or variable distance from the vertical first section where the second section is configured to ride vertically up and down the first section to the desired height for obtaining a radiographic image of a subject. In addition, the support member or column 135 vertical section is rotatable attached to the moveable frame 120 to allow manual rotation of the support member or column 135 around a vertical axis. Height settings for the x-ray tube head 140 can range from low height for imaging feet and lower extremities to shoulder height and above for imaging the upper body portions of patients in various positions.

The perspective view of FIG. 4 shows mobile radiography apparatus 100 in an undocked position for projection imaging, tomosynthesis imaging, or tomographic imaging. Telescoping horizontal section 30 of the support member or column 135 is extendible in a linear direction away from the vertical section of support member or column 135. Mobile radiography apparatus 100 can provide charging for a battery contained in portable radiographic detector 40 inserted into one of the storage slots 134. For example, a charging port in the DR detector 40 may electrically engage a mating power port in one of the storage slots 134 when the DR detector 40 is inserted therein. The mobile radiography apparatus 100 can be also be employed for computed radiography (CR) and/or digital radiography (DR).

Figure 5:
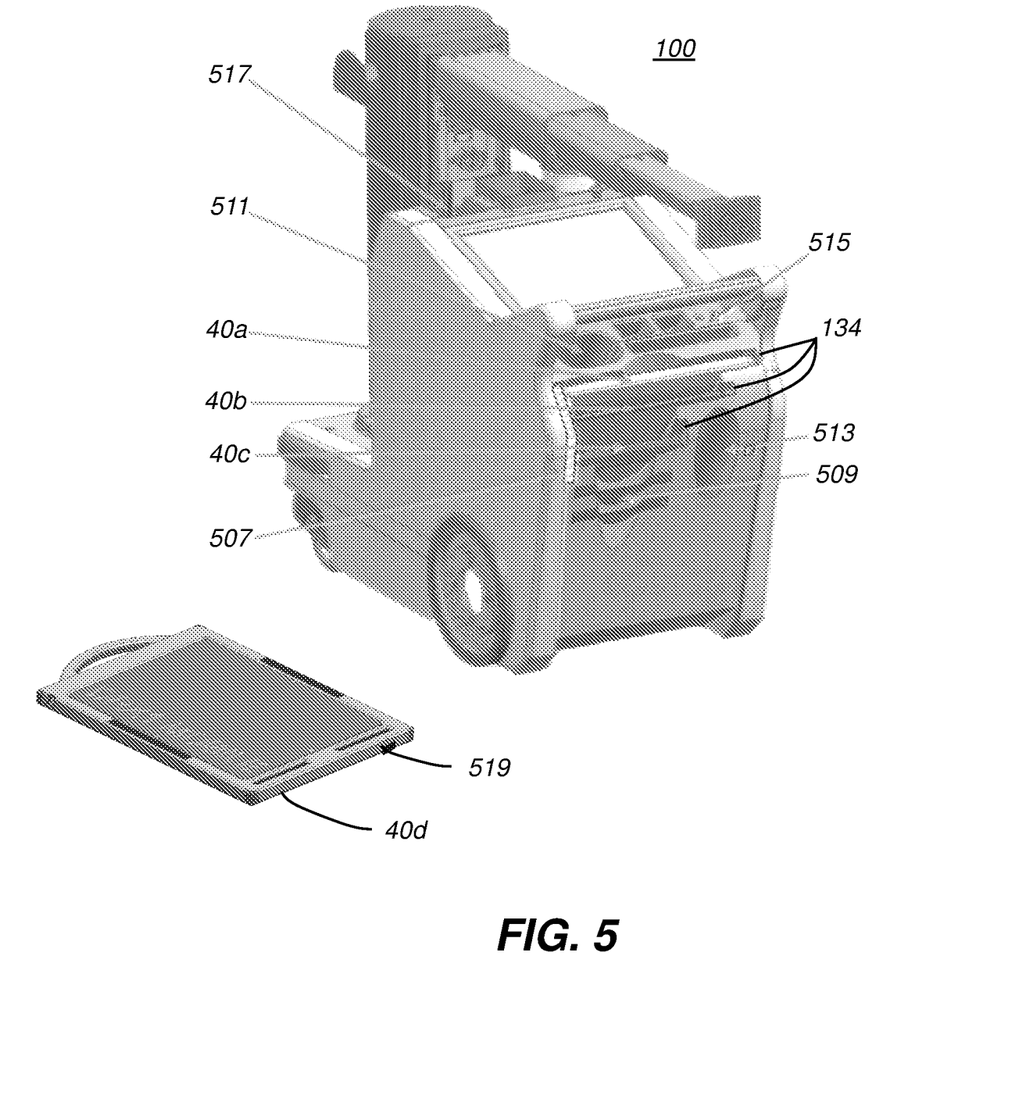
FIG. 5 is a diagram that illustrates the mobile radiography system of FIG. 4 in more detail.

FIG. 5 illustrates mobile radiography apparatus 100 without tube head 140 attached for clarity of description. Portable DR detector storage slots 134 may hold a large portable DR or CR detector 40a, medium size portable CR or DR detector 40b, and small portable CR or DR detector 40c that can be secured within the slots 134 using locking device 507. The locking device 507 can reciprocally move between a first position (e.g., unlocked) where detectors 40 can be removed from the storage slot area 134 area and a second position (e.g., locked) where detectors 40 cannot be removed from the storage slots 134. In one embodiment, the storage slots 134 can include a battery charge slot 509 where at least one battery for use with or removed from a detector 40 can be re-charged by the mobile radiography apparatus 100. One or more additional DR detectors 40d may be associated with mobile radiography apparatus 100. Portable DR detector 40d may be placed in proximity to mobile radiography apparatus 100 such as in a common medical facility x-ray imaging room or it may be carried by a technician intending to use it together with mobile radiography apparatus 100. Each DR detector 40 typically includes a charging port 519 so that the DR detector 40 may have its battery charged when inserted into a storage slot 134. Additional storage areas for materials at the mobile radiography apparatus 100 can include storage 511 for rubber gloves and bag storage area 513. The mobile radiography apparatus 100 can also include a prep/expose control panel 515 and a holder 517 for a wireless remote prep/expose control.

Figure 6:
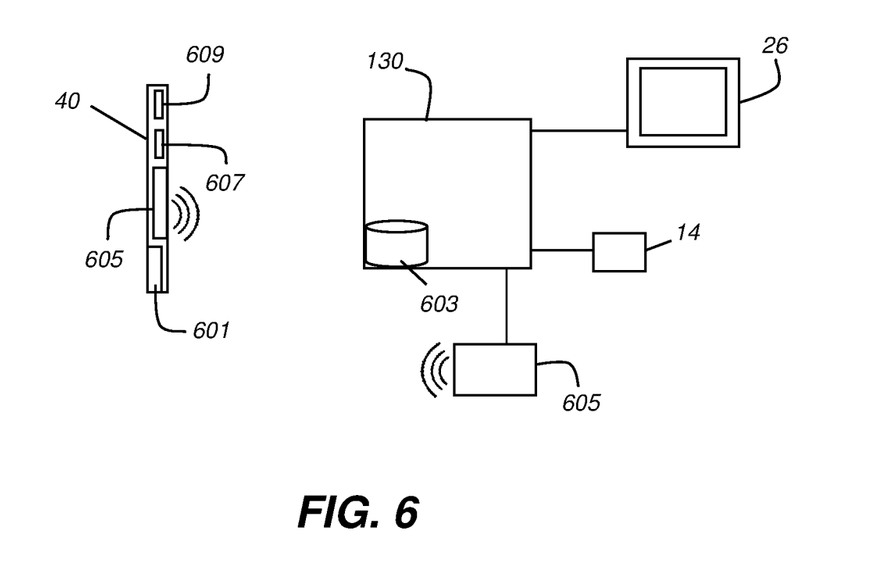
FIG. 6 is a schematic diagram of an exemplary mobile radiography detector management system.
Figure 7:
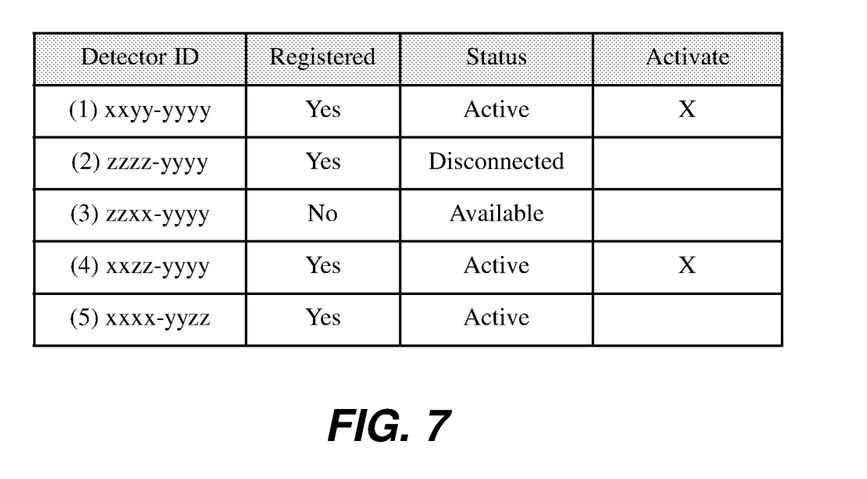
FIG. 7 is an exemplary table of assigned detectors' status.

The schematic block diagram of FIG. 6 shows a system for management of DR detectors 40 used by a particular mobile radiography apparatus 100. Although embodiments described herein refer to mobile radiography apparatuses 100, the invention may be used with stationary in-room x-ray installations that may include x-ray tube cranes fixed to a stationary structure in an x-ray facility and limited to in-room movements, and other fixed position x-ray systems. Mobile radiography apparatus 100 can manage a plurality of associated detectors (e.g., detectors 40a-40d for example). An identifier 601 (ID), which may hardwired in, or assigned and stored in, DR detector 40 provides a unique digital identifier for a particular detector 40 which may be used by detector 40 to determine when a communication, which includes the detector's ID, from mobile radiography apparatus 100 is intended for it, and it may be used by the processing system 130 in mobile radiography unit 100 to target communications to a specific DR detector 40 by including the detector ID in the communication. Identifier 601 may be used to link, register or, as used synonymously herein, assign DR detectors 40 to one or more mobile radiography apparatuses 100 that may travel throughout a medical imaging facility having many portable DR detectors 40 distributed therein and/or one or more stationary in-room x-ray installations. Processing system 130 maintains a registry 603 (as shown, e.g., in FIG. 7) of one or more DR detectors 40 that are associated with mobile radiography apparatus 100, which association may include a previous registration, a current registration, or an available detector 40 that is proximate to the mobile radiography apparatus 100 and can be registered thereto. A detector 40 may transition from a low power mode, sleep mode, or power off state, by waking up the detector 40 or by powering on the detector 40. This may be performed by an operator manually waking or powering on the detector such as by manually activating a switch on the detector. This may also be performed by transmitting a wake up or power on signal from a mobile radiography apparatus 100 to the DR detector 40. This may also be performed by a signal from an on-board accelerometer in the detector 40 responding to sensing movement of the detector 40. Upon awakening or powering on in this way, the detector 40 transmits an "available" signal. Upon receiving the availability signal and a detector ID, mobile radiography apparatus 100 may then add the detector 40 to a registry of available detectors stored at the mobile radiography apparatus 100, as shown in FIG. 7. Registry 603 can include electronic memory for storage of power level, registration information and other status information about one or more identified DR detectors 40 that are programmed to transmit such information.

In one embodiment, processing system 130 may be programmed to automatically register a detector 40 that is detected to be available and in proximity to mobile radiography apparatus 100. The processing system 130 may detect that an unregistered detector 40 is in proximity to the mobile radiography apparatus 100, such as by using a near field communication protocol, such as bluetooth modules 605. Upon detecting the proximate DR detector 40, mobile radiography apparatus 100 may determine that the proximate detector 40 is compatible with mobile radiography apparatus 100, or the mobile radiography apparatus 100 may query the proximate DR detector for an identifier 601, or other DR detector system information, to determine compatibility. If the proximate DR detector 40 is determined to be compatible, mobile radiography apparatus 100 may proceed with registering the DR detector 40, whereafter the proximate DR detector 40 may be used together with mobile radiography apparatus 100 to capture radiographic images of a subject, if designated to do so.

In one embodiment, registering a DR detector 40 in system registry 603 may be performed by operator entry at an input screen 110 of mobile radiography apparatus 100. Registration of a DR detector 40 may be used to enable certain status communications between registered detectors 40 and mobile radiography apparatus 100, such as to validate that data is being communicated only from an appropriate compatible DR detector 40 so that only data from a registered DR detector 40 is transferred to processing system 130. System 130 can have multiple DR detectors 40 registered therewith, but can be configured to communicate only with one designated DR detector 40 at a time. However, this may result in certain operator errors as described herein, which may be avoided by implementing the embodiments disclosed herein. Thus, a registry 603 of available DR detectors 40 can be maintained at processing system 130 so that one detector 40, a portion of the detectors 40, or all detectors 40 can be activated for a particular x-ray imaging examination. System 130 can maintain power level information, calibration files or other information for a number of DR detectors 40 in the registry 603, from which designated DR detectors 40 for a particular examination can be selected for activation, as shown in the last column of FIG. 7. Deregistration can also be used to deregister a particular DR detector 40 with respect to mobile radiography apparatus 100.

FIG. 7 is an exemplary table that may be electronically stored in registry 603 which lists a number of detectors 40 that are associated with an x-ray imaging system, such as mobile radiography system 100. Table information signifying that a detector 40 is registered and powered on, or awake, may be configured to indicate to the processing system 130 that these detectors are active, proximate to the mobile radiography system 100, and can be immediately activated for x-ray exposure image capture. Table information signifying that a detector 40 is registered and disconnected may be configured to indicate to the processing system 130 that such registered detectors are inactive, such as being powered off, in a low power sleep mode, or too distant from the mobile radiography apparatus 100 in order to communicate therewith. Table information signifying that a detector 40 is not registered but available may be configured to indicate to the processing system 130 that these detectors are proximate to the mobile radiography apparatus 100 and can be registered thereto, if desired. The processing system 130 may be selectively configured to designate any one of detectors (1), (4) and (5) in the table, or a combination thereof, as active detectors that may be immediately activated for capturing x-ray images in response to exposure synchronization signals transmitted from processing system 130, as exemplified in the last column of FIG. 7. As the terms "activate", "activated" or "activation" are used herein, a detector 40 is activated when it is awaiting a signal, such as one or a sequence of synchronization signals, from the mobile radiography apparatus 100, which causes the detector 40 to open its integration window, for a preset period of time, to capture x-ray signals emitted by an x-ray source and impacting the detector 40, if any. If the processing system 130 is configured to automatically register detectors that are available to be registered, then detector (3) in the table of FIG. 7 may be registered and added to the combination of active DR detectors designated for activation.

A problem that may occur during x-ray imaging where a number of different DR detectors 40 is available to an operator is that radiographic images may not be properly captured during x-ray exposure because of a mismatch between the detector 40 being used by the operator for image capture and the detector 40 actually activated for capturing the exposures. Thus, in one embodiment, activation of all DR detectors 40 that are available to an imaging system can be performed to avoid this problem. In one embodiment, an operator may begin initialization of the mobile radiography apparatus 100 for an x-ray examination, such as by setting a power level of the x-ray source, turning on a remote control for firing the x-ray source, displaying an examination schedule for a patient on a display 110, 110', accessing technique information for a particular x-ray examination, etc. In response to these detected operator actions, the processing system 130 may be configured to automatically access the registry 603 to identify registered and active DR detectors and to transmit a detector activation signal to some or all of the identified DR detectors. Thus, if all available detectors are activated in response to the activation signal, any detector that is used by an operator will properly capture x-ray images, as intended.

In one embodiment, activation of some or all detectors 40 registered to mobile radiography apparatus 100, may be initiated by one, or a combination, of several user actions in addition to the mobile radiography apparatus 100 detecting the operator actions described above: 1) removal of detector 40 from a storage slot; 2) detecting detector movement using a built-in accelerometer; and 3) a proximity sensor detecting that the detector is moving away from a storage location or from the mobile radiography apparatus 100. In one embodiment, the detector 40 is configured to send a system activation signal to the processing system 130 when the detector 40 detects that its charging port is disengaged from a mating power port in the storage slot 134. In one embodiment, the detector 40 can be configured to send a system activation signal to the processing system 130 when the detector 40 detects movement, such as using a signal from an on-board three dimensional accelerometer 607 (FIG. 6). In one embodiment, the detector 40 is configured to send a system activation signal to the processing system 130 when the detector 40 detects that it is being moved away from a storage location, such as a storage slot 134 in the mobile radiography imaging apparatus 100 or a storage bin in an x-ray examination room, by using an on-board proximity sensor 609 (FIG. 6). Such a proximity sensor may also be linked to the detector's bluetooth module 605 to measure a weakening signal strength therein in relation to the bluetooth module 605 in the mobile radiography apparatus 100, in order to determine increasing distance, or movement, away from mobile radiography apparatus 100. In response to receiving such a system activation signal, the processing system 130 may be configured to automatically access the registry 603 to identify active DR detectors and to activate some or all active registered detectors 40 by transmitting a detector activation thereto. In one embodiment, the processing system 130 may be configured to transmit a power on or wake-up signal to detectors 40 that are listed in the registry 603 as disconnected. Thus, activating the detectors 40 would include powering on or awakening particular detectors 40 from an idle mode, a low power sleep mode, or even a power off state, to an active state, in order to be activated for capturing image data during an x-ray exposure. In one embodiment, disconnected detectors 40 and available unregistered detectors 40 may all be automatically registered and rendered active such that all the detectors in a registry 603 may be designated for immediate activation to capture x-ray exposures.

Figure 8:
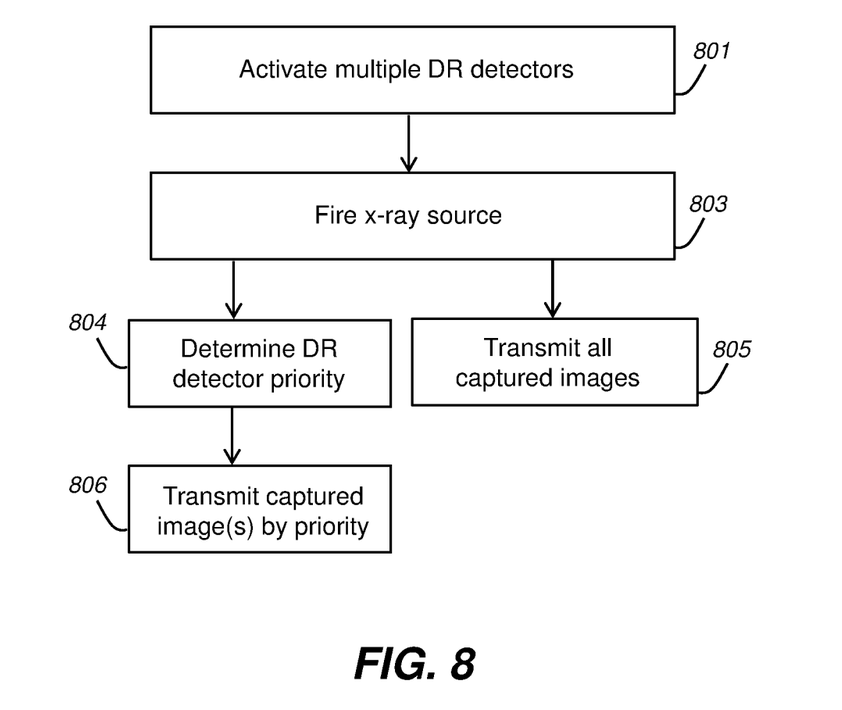
FIG. 8 is a flowchart for operating an x-ray imaging system.

FIG. 8 is a flowchart for operating an x-ray imaging system, such as mobile radiography system 100, having multiple activated DR detectors. After activating multiple detectors in step 801, the x-ray imaging system fires an x-ray source in step 803 to generate an image of a subject for capture by an activated DR detector 40. In step 804, an automated procedure is undertaken to determine which one or more DR detectors 40 has captured a suitable diagnostic x-ray image of the subject. During this step 804, each activated DR detector 40 is programmed to automatically, after closing its integration window, or in response to a request from the x-ray imaging system, determine an image rating of the just captured x-ray image and transmit the rating to the x-ray imaging system, such as the mobile radiography apparatus 100. In one embodiment, the image rating may be determined by programming each activated DR detector to calculate and transmit a numerical average signal level of the detector's pixels, which calculated average signal level may be used as the image rating. In one embodiment, the image rating may be determined by programming each activated DR detector to record and transmit a maximum signal level as captured in the detector's pixels, which maximum signal value may be used as the image rating. In one embodiment, the image rating may be determined by programming each activated DR detector to calculate and transmit a numerical average signal level of exposed pixels in a preselected region of the detector 40, such as a central region of the detector 40, which calculated average region signal level may be used as the image rating. This embodiment may be useful when a collimator is used to expose a small area of the detector 40. In one embodiment, the image rating may be determined by programming each activated DR detector to calculate and transmit a percentage of pixels of the detector that satisfy a logical comparison to a preset signal level, which calculated percentage may be used as the image rating. In one embodiment, the image rating may be determined by programming each activated DR detector to store and transmit a time at which its on-board accelerometer last detected movement, which time of detected movement may be used by the imaging system to determine the detectors' image ratings. Other suitable image rating methods may be used as well.

Figure 9:
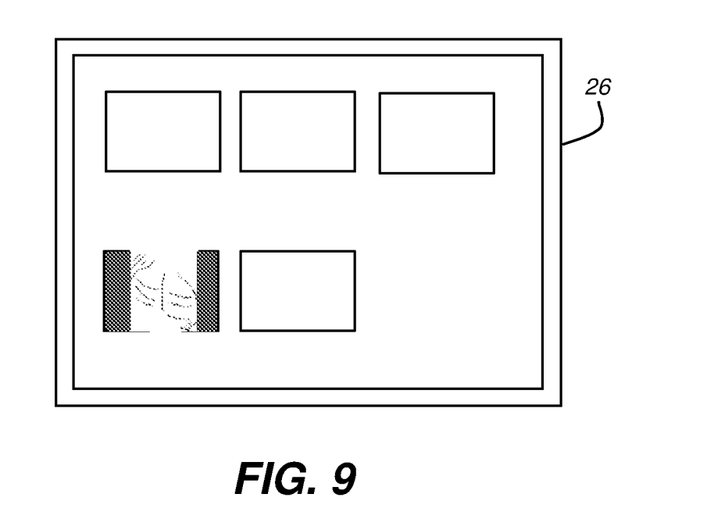
FIG. 9 is a display of exposed images from DR detectors.

In step 806, the image ratings may be used by the imaging system to determine a priority order for the detectors 40 to transmit captured image data. The imaging system, such as mobile radiography system 100, may rank the image ratings from highest to lowest values, or vice versa, or may use some other ranking method. If the time of accelerometer movement is used for image ratings, the imaging system, such as mobile radiography system 100, may rank the image ratings from most recent time of movement to least recent time of movement, or vice versa. In one embodiment of step 806, the received image ratings from all activated DR detectors may be used by the imaging system, such as mobile radiography system 100, to determine which one of the activated DR detectors captured image is transmitted to the imaging system for diagnostic purposes. In one embodiment, the image, or detector, at the top of the ranking may be selected for transmission of the captured image for diagnostic purposes. In one embodiment of step 806, the received image ratings from all activated DR detectors may be used by the imaging system, such as mobile radiography system 100, to determine a priority order of the activated DR detectors 40 in which to transmit some or all of the captured images to the imaging system for diagnostic purposes. The priority order may be used to transmit only the first, highest ranking priority image, a plurality of the highest priority ranked images, or all of the captured images. In one embodiment, an alternative method to steps 804, 806, which follow step 803, is step 805, in which each activated DR detector is programmed to automatically, or in response to a request from the x-ray imaging system, transmit its captured x-ray image without regard to a priority order to the x-ray imaging system, such as the mobile radiography apparatus 100. The imaging system may then immediately display all the transmitted captured images so that an operator of the x-ray imaging system may select the most appropriate image for diagnostic purposes. In one embodiment, as shown in FIG. 9, all the transmitted captured images may be immediately displayed on an electronic display 26 as thumbnail images, from which an operator may select the most appropriate image for diagnostic purposes.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data, processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A radiography system comprising:
an x-ray source;
a plurality of DR detectors assigned to the radiography system and each configured to capture an image in synchronization with one activation of the x-ray source; and
a controller configured to transmit a detector activation signal to activate the plurality of assigned DR detectors and to transmit a source activation signal to activate the x-ray source,
wherein the plurality of DR detectors are further configured to each transmit to the radiography system the image captured therein in synchronization with the one activation of the x-ray source,
wherein each of the plurality of DR detectors is further configured to transmit a preparation signal to the controller in response to a corresponding sensor indicating that the detector is being prepared for an x-ray image capture, and wherein the controller is further configured to transmit the detector activation signal in response to receiving the preparation signal, and
wherein the corresponding sensor indicating that the detector is being prepared for an x-ray image capture comprises an accelerometer for detecting movement of the detector.

2. The system of claim 1, further comprising a controller, wherein each of the plurality of detectors are further configured to evaluate the image captured by the detector and to transmit an evaluation value corresponding thereto to the controller, a priority order is determined by the controller according to the evaluation values received from of each of the plurality of detectors, and wherein the controller controls the plurality of detectors to each transmit to the radiography system the image captured therein according to the priority order.

3. The system of claim 2, wherein each of the plurality of detectors are further configured to calculate the corresponding evaluation value based on a signal level of pixels in the captured image.

4. The system of claim 1, wherein the controller is further configured to determine that an operator is preparing the system for acquiring an x-ray image and to transmit the detector activation signal in response thereto.

5. A method of operating a radiography system comprising an x-ray source and a plurality of DR detectors, the method comprising:
firing the x-ray source and simultaneously capturing an image in each of the plurality of DR detectors;
determining which one of the plurality of detectors most recently sensed its own movement; and
transmitting from the one detector which most recently sensed its own movement the image captured therein.

6. The method of claim 5, further comprising each of the plurality of detectors evaluating the image captured therein and transmitting an evaluation value corresponding thereto.

7. The method of claim 6, further comprising each of the plurality of detectors determining a signal level in one or more pixels of the detector to perform the step of evaluating the image captured therein.

8. The method of claim 5, further comprising:
- at least one of the plurality of detectors sensing that it is being prepared for image capture, and, in response, transmitting a detector preparation signal; and
- transmitting an activation signal to activate the plurality of DR detectors in response to receiving the detector preparation signal.

9. The method of claim 8, wherein the step of sensing comprises receiving a signal from an on-board accelerometer indicating that the detector is being moved.

10. The method of claim 5, further comprising the radiography system detecting the system being prepared to capture a radiographic image and, in response, transmitting an activation signal to activate the plurality of DR detectors.

11. The method of claim 5, further comprising all of the plurality of DR detectors transmitting the image captured therein in a sequential order.

* * * * *